United States Patent [19]

Danby et al.

[11] Patent Number: 4,477,054
[45] Date of Patent: Oct. 16, 1984

[54] PRECISION VALVE ASSEMBLY

[75] Inventors: Hal C. Danby, Palo Alto; Werner W. Ciupke, San Mateo, both of Calif.

[73] Assignee: Anatros Corporation, San Jose, Calif.

[21] Appl. No.: 431,312

[22] Filed: Sep. 30, 1982

[51] Int. Cl.³ .................... F16K 31/524; F16K 7/16
[52] U.S. Cl. .................... 251/122; 251/254; 251/256; 251/252; 604/246
[58] Field of Search ............ 251/252, 254, 256, 262, 251/121, 122, 331; 604/246

[56] References Cited

U.S. PATENT DOCUMENTS

| | | | |
|---|---|---|---|
| 2,087,356 | 7/1937 | Parker | 251/256 X |
| 3,278,155 | 10/1966 | Jehn | 251/254 |
| 3,819,148 | 6/1974 | Cole et al. | 251/252 |

*Primary Examiner*—Arnold Rosenthal
*Attorney, Agent, or Firm*—William B. Walker

[57] ABSTRACT

A precision valve assembly for controlling flow of fluids to a patient having a valve element mounted on a diaphragm. At least one ball positioned in a spiral track, when moved toward the center by relative rotation of the spiral track and an opposed longitudinal track, brings a valve and valve seat together to restrict fluid flow therethrough.

11 Claims, 9 Drawing Figures

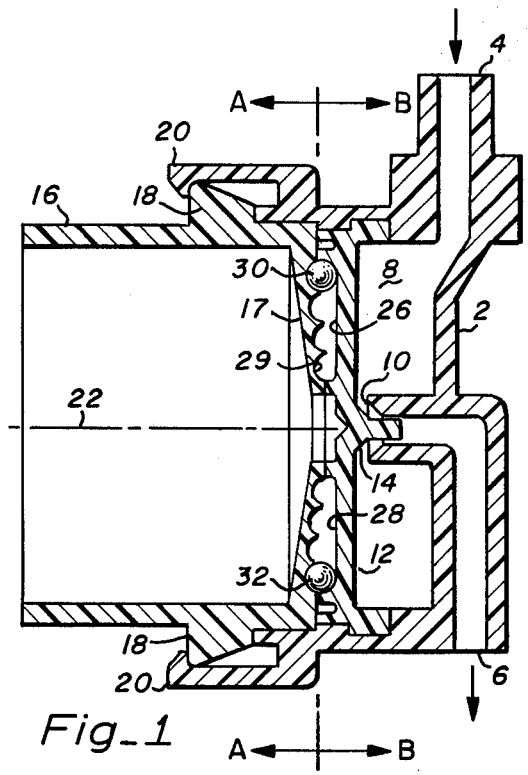
Fig_1  Fig_2  Fig_3  Fig_4

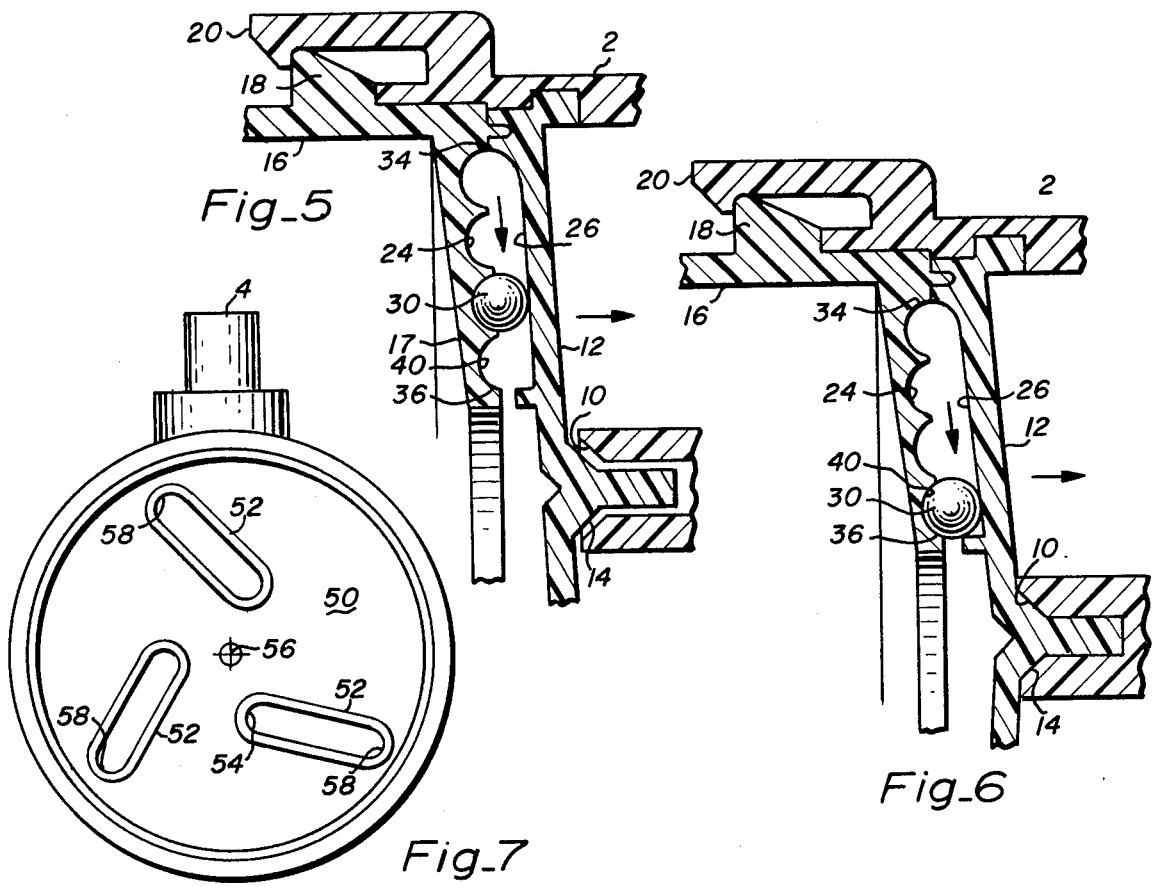
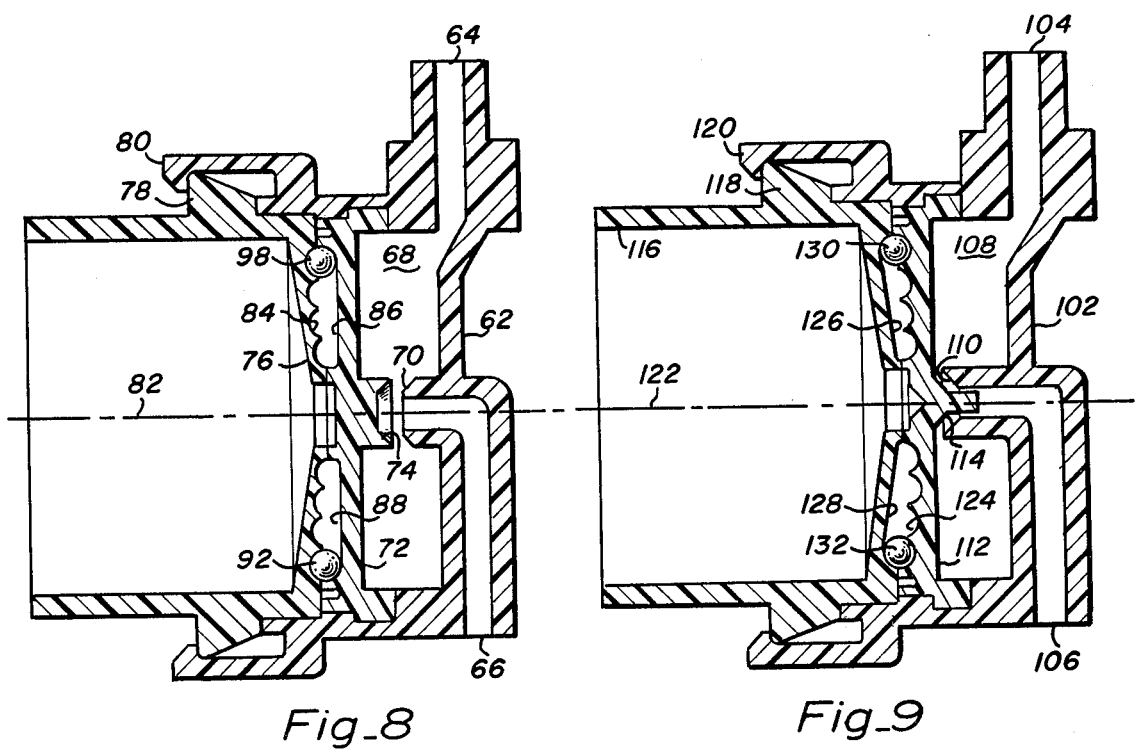

PRECISION VALVE ASSEMBLY

Field of the Invention

This invention relates to a precision valve assembly which can be used for accurately controlling the flow of fluids delivered to a patient. More specifically, it relates to a precision valve assembly which is particularly suitable for use in conjunction with volumetric control monitors used with fluid administration sets to deliver exact amounts of parenteral and other fluids to patients at precise flow rates.

Background of the Invention

DESCRIPTION OF THE PRIOR ART Medical patients in and out of the hospital frequently require continuous administration of parenteral and other fluids, and these must often be infused at precise, controlled flow rates. Traditionally, an attendant has adjusted a pinch clamp mounted on flexible, plastic tubing to provide a desired drop rate. The conformation of the flow passageway of the pinched tubing is not constant and gradually changes due to plastic creep and hoop tension. To compensate for these changes and avoid a variable flow rate, an attendant must periodically readjust the clamp setting to obtain the desired drop rate.

A variety of flow controllers have been devised which adjust the flow rate of parenteral fluids by automatically operating a pinch clamp or other valve assembly in response to drop rate changes as determined by photoelectric methods. Each drop falls through and interrupts a beam of light, the interruptions are counted, and the count is compared with a desired count. Such a counter is disclosed in U.S. Pat. No. 4,014,010, systems responsive to such a counter are described in U.S. Pat. Nos. 4,204,538 and 4,207,871.

The flow systems and counters disclosed in the above patents require constant adjustment because of the limitations of the valve assembly, making necessary a large electric energy supply. Portable units are then unduly bulky because of the large battery size. The prior art units tend to be heavy, complex and require operating voltages which are undesirable in a hospital environment, further detracting from their usefulness, particularly as applied to ambulatory patients.

U.S. Pat. No. 3,396,939 discloses a valve structure incorporating a frustuconical member which seats on a valve seat in response to the rotation of portions of the valve assembly. U.S. Pat. No. 2,806,654 discloses a control valve including ball elements. The balls travel in radial tracks and activate a snap action mechanism which in turn drives a valve member to a closed position. These patents are directed to off-on valves used in high pressure systems. Although the prior art valves have elements common with the valve assembly of this invention, they do not operate in the same manner or with the same precision.

SUMMARY AND OBJECTS OF THE INVENTION

It is an object of this invention to provide a precision valve assembly which is compact, provides a more precise control of fluid therethrough using a minimal amount of energy, and is suitable for use in parenteral infusion systems in a hospital environment.

It is a further object of this invention to provide a lightweight, inexpensive, disposable precision control valve assembly which can be operated either manually or in automatic systems for fluid infusion in a hospital environment.

In summary, the precision valve assembly of this invention comprises a valve and a cooperating valve seat aligned therewith, either the valve or the valve seat being mounted on a diaphragm. At least one ball and preferably two balls are positioned between facing track elements having distal and proximal ends with respect to a central axis. One track element has a spiral configuration, and the other track element comprises one and preferably at least two longitudinal tracks, the proximal end being closer to the central axis than the distal end thereof. One of the track elements is mounted on the diaphragm. The distance between the proximal ends of the track elements is less than the diameter of the ball positioned therebetween when the ball is positioned at the distal end, thereby defining a wedge configuration. When one of the track elements is rotated with respect to the other about the central axis, each ball is displaced along the tracks from the distal ends to the proximal ends thereof or in the reverse direction. As a result of the mutual wedge configuration of the tracks, the diaphragm is displaced in an axial direction as each ball is driven toward the center, that is, from the distal ends toward the proximal ends of the tracks. Reverse rotation causes each ball to move in a reverse direction, permitting movement of the diaphragm in the reverse axial direction. The valve element mounted on the diaphragm is thereby displaced axially toward or away from its counterpart valve elements, restricting or increasing fluid flow therethrough accordingly.

In the preferred embodiments of the precision valve assembly of this invention, the valve element is preferably mounted on the diaphragm and at least two logitudinal track elements are preferably mounted in a balanced (symmetrical) arrangement on the diaphragm means. At least one ball is preferably provided in each longitudinal track. The diaphragm is preferably made from a flexible material such as a flexible plastic. The spiral track element preferably terminates in circular tracks at the proximal and distal ends thereof.

Still further objects and important aspects of the precision valve assembly of this invention will be apparent from the more detailed description provided hereinafter.

Brief Description of the Drawings

FIG. 1 is a cross-sectional view of a precision valve assembly of this invention.

FIG. 2 is a cross-sectional view of the precision valve assembly of FIG. 1 taken along lines A—A.

FIG. 3 is a cross-sectional view of the precision valve assembly of FIG. 1 taken along lines B—B.

FIGS. 4, 5, and 6 are fragmented, cross-sectional views of a precision valve assembly of this invention showing the valve in the open, intermediate and closed positions, respectively.

FIG. 7 shows a cross-sectional view of an embodiment of the precision valve assembly of this invention with an alternate longitudinal track configuration mounted on the diaphragm element.

FIG. 8 is a cross-sectional view of a precision valve embodiment of this invention wherein the longitudinal tracks on the diaphragm element are inclined with respect to the spiral tracks.

FIG. 9 is an embodiment of the precision valve assembly of this invention wherein the spiral track is mounted on the diaphragm element, and longitudinal track elements are mounted on the rotary element opposed thereto.

Description of the Preferred Embodiments

Referring to FIG. 1, a cross-sectional view of a precision valve assembly of this invention is shown. The valve housing 2 has an inlet port 4 and an outlet port 6 therein. The inlet port 4 communicates with the outlet port 6 by way of chamber 8 and valve seat 10. Diaphragm 12 having valve 14 mounted thereon is aligned with the valve seat 10 so that the frustuconical surface of the valve element 14 can cooperate with the valve seat 12 to provide a variable restriction to fluid flow therethrough. Diaphragm 12 is preferably made from a flexible material, optimally a flexible thermoplastic polymer such as acetal polymers and copolymers, nylon, polycarbonates, high density polyethylene, polypropylene, and the like.

Rotary element 16 has an outer rim 18 which forms a latching engagement with the housing latch 20. The rotary element 16 is mounted for rotation with respect to the diaphragm element 12 about central axis 22.

The opposed surfaces of the rotary element 16 and diaphragm 12 define a longitudinal track and spiral track combination within which balls 30 and 32 are positioned for movement. In the embodiment shown in FIG. 1, a spiral track 24 is formed by the backstop member surface 17 of the rotary element 16. Longitudinal tracks 26 and 28 are mounted on or defined by the surface of diaphragm 12. The balls 30 and 32 positioned in the longitudinal and spiral tracks function as spacers between the longitudinal and spiral tracks. The thickness of backstop member 17 is greatest at its periphery and gradually decreases toward its center. The thickness is smallest adjacent its center to provide controlled flexibility. In general, the diaphragm is more flexible than the backstop member 17. If because of manufacturing variances, the valve components 10 and 14 completely close before the balls 30 have reached the inner track 40 (shown in FIG. 2), continued rotation of rotary element 16 will cause continued movement of the balls 30 toward the center and increase pressure on the diaphragm and valve assembly. By providing some flexibility in the backstop member 17, such strains are relieved.

Referring to FIG. 2, a cross-sectional view taken along the lines A—A in FIG. 1 is shown. This view, taken in the direction of the rotary element 16 shows the configuration of spiral track 24 in greater detail. Spiral track 24 has a distal end 34 which is distally positioned with respect to the central axis 22 and a proximal end 36 which is proximate the center axis 22. The distal portion 34 of the spiral track 24 defines a circular groove 38, and the proximal portion 36 of the spiral track 24 defines a circular groove 40. When a ball travels to the distal limit of the spiral, it moves into circular track 38 and further clockwise rotation of the rotary element 16 does not stress the distal wall 34 of the track. Likewise, when a ball travels to the proximal limit of the spiral track 24 it moves into circular track 40, and further counter-clockwise rotation of the rotary element 16 does not stress the proximal wall 36 of the track.

Guide portion 42 is a low relief distal continuation of the spiral which with the projection 43 displaces the ball from the circular track portion into the spiral track portion and toward the axial center 22 when the rotary element is turned in a counter-clockwise direction with respect to FIG. 2. The guide portion 44 is a low relief proximal continuation of the spiral groove 40 which with projection 45 displaces the ball from the circular track portion into the spiral track portion and away from the axial center 22 when the rotary element 16 is turned clockwise in the configuration shown in FIG. 2. Two balls are shown in the embodiment illustrated in FIG. 1. The device will operate with only one ball or with a plurality of balls including more than one ball in each longitudinal track. The preferred number of balls is one ball in each longitudinal track.

Referring to FIG. 3, a cross-sectional view of the precision valve assembly of FIG. 1 taken along lines B—B is shown. In this embodiment, more details are shown of the diaphragm element 12 and the longitudinal grooves 26 and 28.

The longitudinal tracks 26 and 28 are shown in a radial configuration in a plane perpendicular to the central axis 22 and extending from their proximal ends 46 and 48 radially outward to the distal ends 50 and 52, respectively.

In the embodiment shown in FIG. 1, the spiral tracks shown in greater detail in FIG. 2 are formed on a frustuconical surface and form a wedge construction in conjunction with the longitudinal tracks on the planar surface shown in detail in FIG. 3. The distance between the spiral track and the longitudinal tracks decreases as the proximal end is approached from the distal edge of the spiral track.

FIGS. 4, 5, and 6 are fragmentary cross-sectional views of the embodiment of this invention shown in FIG. 1 illustrating the operation of the precision valve assembly. In the configuration shown in FIG. 4, the ball 30 is shown in the circular track 38 at the distal edge 34 of the spiral track. The valve 14 is in the position maximally displaced from the valve seat 10 whereby maximum fluid flow is obtained. As the rotary element 16 is rotated, the ball 30 is forced by the sidewall of the longitudinal track 26 along the spiral track, travelling from the distal end 34 toward the proximal end 36 in response to the rotary motion. Because the spiral track 24 is on a frustuconical surface and forms a wedge with the planar diaphragm 12, the bal displaces the flexible diaphragm 12 and valve element 14 mounted thereon in an axial direction toward the valve seat 10 as is moves toward the center. This precisely and gradually closes the space between the valve surface 14 and the valve seat 10. FIG. 5 shows the ball 38 in an intermediate position with the valve opening partially restricted. In the opposite extreme position shown in FIG. 6, the ball 36 has been forced against proximal edge 36 and into the circular track 40 adjacent to center axis 22, and the diaphragm 12 and the valve element 14 mounted thereon has been pressed against the valve seat 10, thereby completely terminating fluid flow. Reversing the rotational direction of rotary element 16 causes the reverse to occur. The side wall of the longitudinal track 26 moves the ball into the spiral track 24 causing it to travel from the proximal end toward the distal end. As the ball moves in the distal direction, the flexible diaphragm 12 and valve 14 retract in an axial direction from the valve seat 14, gradually and precisely opening the valve as the ball moves.

It can thus be seen, that the rotary motion of rotary element 16 is translated into a very small, highly precise axial motion of the valve element 14 with respect to the valve seat 10, giving a high degree of control. In the embodiment described immediately above, the flexible diaphragm 12 functions in a resilient manner to retract to its original unflexed position as the displacement of ball 30 permits this movement.

Referring to FIG. 7, an alternate diaphragm embodiment is shown. Diaphragm 50 has three longitudinal tracks 52 mounted thereon, each having a proximal end 54 evenly spaced about a center axis 56 and having distal ends 58 evenly spaced about the center axis 56 in a balanced configuration. In this embodiment, the longitudinal tracks are shown disposed at an angle to the radius in a plane perpendicular to the center axis 56, that is, the proximal ends 54 are nearer the center axis 56 than the distal ends 58. This reduces track wall stress. Optionally, a ball is positioned in each track, but the invention is not limited thereto for it can operate with a ball in only one of the three tracks, or with one or more balls in each of the tracks.

Referring to FIG. 8, a cross-sectional view of an alternate embodiment of the precision valve assembly of this invention is shown. The valve housing 62 has an inlet port 64 and an outlet port 66 therein. The inlet port 64 communicates with the outlet port 66 by way of chamber 68 and valve 70. Diaphragm 72 having valve seat 74 mounted thereon is aligned with the valve 70 so that the frustuconical surface of the valve 70 can cooperate with the valve seat 74 to provide a variable restriction to fluid flow therethrough. Diaphragm 72 is preferably made from a flexible material, optimally a flexible or resilient plastic polymeric material such as natural or synthetic rubber or highly plasticize polyvinyl chloride.

Rotary element 76 has an outer rim 78 which forms a latching engagement with the housing latch 80. The rotary element 76 is mounted for rotation with respect to the diaphragm element 72 about central axis 82.

The opposed surfaces of the rotary element 76 and diaphragm 72 define a longitudinal track and spiral track combination within which balls 90 and 92 are positioned for movement. In the embodiment shown in FIG. 7, a spiral track 84 is formed by the surface of the rotary element 76. Longitudinal tracks 86 and 88 are mounted on or defined by the surface of diaphragm 72. The balls 90 and 92 positioned in the longitudinal and spiral tracks function as spacers between the longitudinal and spiral tracks.

In this embodiment, the longitudinal tracks 86 and 88 are inclined with respect to a plane perpendicular to the central axis 82 to form a wedge configuration along the radial direction in conjunction with the spiral track 84. Spiral track 84 is formed on a plane. Rotation of rotary element 76 drives balls 90 and 92 along the spiral track 84. Movement of the balls toward the central axis 82 effects translation of the diaphragm 72 and the valve seat 74 thereon in an axial direction toward the valve 70, causing restriction of the valve and reduction of fluid flow therethrough. Rotation of rotary element 76 in an opposite direction moving the balls 90 and 92 outward from the central axis 82 causes movement of the diaphragm 72 and the valve seat 74 in the opposite direction, increasing fluid flow. The operation of the valve assembly is essentially the same as described above with respect to the embodiment shown in FIG. 1.

Referring to FIG. 9, a still further embodiment of this invention is shown in cross-section. The valve housing 102 has an inlet port 104 and an outlet port 106 therein. The inlet port 104 communicates with the outlet port 106 by way of chamber 108 and valve seat 110. Diaphragm 112 having valve 114 mounted thereon is aligned with the valve seat 110 so that the frustuconical surface of the valve element 114 can cooperate with the valve seat 112 to provide a variable restriction to fluid flow therethrough.

Rotary element 116 has an outer rim 118 which forms a latching engagement with the housing latch 120. The rotary element 116 is mounted for rotation with respect to the diaphragm element 112 about central axis 122.

The opposed surfaces of the rotary element 116 and diaphragm 112 define a longitudinal track and spiral track combination within which balls 130 and 132 are positioned for movement. In the embodiment shown in FIG. 9, spiral track 124 is formed on or by the surface of the diaphragm 112. Longitudinal tracks 126 and 128 are mounted on or defined by the surface of the rotary element 116. The balls 130 and 132 positioned in the longitudinal and spiral tracks function as spacers between the longitudinal tracks 126 and 128 and the spiral track 124. In the embodiment shown in FIG. 9, the longitudinal tracks 126 and 128 on the rotary element 116 are inclined or form an angle with respect to a plane perpendicular to the central axis 122, thereby forming a wedge with respect to the planar diaphragm 112 and the spiral track 124 thereon. Rotation of the rotary element 116 drives balls 130 and 132 along the spiral track 124. As described with respect to the embodiments of FIGS. 1 and 8, movement of the balls toward the central axis 122 effects translation of the diaphragm 112 and valve 114 toward the valve seat 110, restricting the valve and reducing the fluid flow therethrough. Opposite rotation of the rotary element 116 and movement of the balls 130 and 132 away from the central axis 122 causes movement of the diaphragm 112 and valve 114 away from the valve seat 110, increasing fluid flow therethrough. The operation of this valve assembly is the same as described above with respect to the embodiment shown in FIG. 1.

The components of the precision valve assembly of this invention can be made of any standard inert materials and are preferably made of polymeric plastics which can be cast or injection molded.

The invention claimed is:

1. A precision valve assembly comprising a valve means and a valve seat means aligned therewith, one of said valve means and valve seat means being mounted on a diaphragm means, at least one ball positioned between opposed track elements which comprise a spiral track having a distal end and a proximal end with respect to a central axis and at least one longitudinal track having a distal end further from said central axis than a proximal end, the distance between the proximal ends of the spiral and longitudinal tracks being less than the outer diameter of the ball when the ball is positioned distally from the central axis, one of said track elements being mounted on the diaphragm means, the ball comprising means for displacing the track mounted on the diaphragm means and the valve element mounted thereon in an axial direction when the tracks are rotated with respect to each other about the central axis and a ball is moved along the tracks.

2. The precision valve assembly of claim 1 wherein the longitudinal track is mounted on the diaphragm means.

3. The precision valve assembly of claim 2 wherein at least two longitudinal tracks are mounted on the diaphragm means in a balanced configuration, and at least one ball is positioned in each track.

4. The precision valve assembly of claim 3 wherein the diaphragm means is flexible.

5. The precision valve assembly of claim 1 wherein the spiral track terminates in circular tracks at its proximal and distal ends.

6. The precision valve assembly of claim 1 wherein the spiral track converges toward the longitudinal track element at the proximal end thereof.

7. The precision valve assembly of claim 6 wherein the longitudinal track defines a path on a frustuconical surface converging in an axial direction toward the spiral track at the proximal end thereof.

8. The precision valve assembly of claim 6 wherein the spiral track element defines a path on a frustuconical surface converging in an axial direction toward the longitudinal track at the proximal end thereof.

9. The precision valve assembly of claim 8 wherein at least two longitudinal track elements are mounted on the diaphragm means in a balanced configuration.

10. The precision valve assembly of claim 9 wherein the diaphragm means is flexible.

11. The precision valve assembly of claim 10 wherein the spiral track terminates in circular tracks at the proximal end and the distal end thereof.

* * * * *